Figure 1:
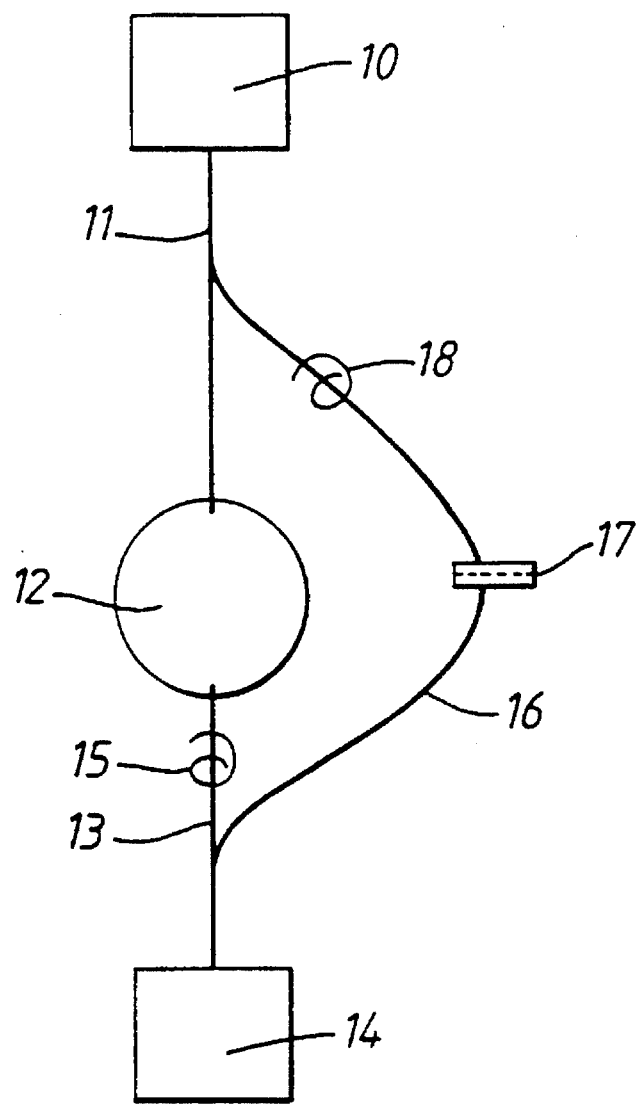

United States Patent [19]

Page et al.

[11] Patent Number: 5,601,730

[45] Date of Patent: Feb. 11, 1997

[54] PROCESS AND APPARATUS FOR REMOVAL OF UNWANTED FLUIDS FROM PROCESSED BLOOD PRODUCTS

[75] Inventors: Roger E. Page, Hayling Island; Keith S. Morris, Emsworth; Graham D. Lowe, Hayling Island, all of United Kingdom; Vlado I. Matkovich, Glen Cove, N.Y.

[73] Assignee: Pall Corporation, East Hills, N.Y.

[21] Appl. No.: 392,884

[22] PCT Filed: Sep. 1, 1993

[86] PCT No.: PCT/GB93/01849

§ 371 Date: Mar. 21, 1995

§ 102(e) Date: Mar. 21, 1995

[87] PCT Pub. No.: WO94/05344

PCT Pub. Date: Mar. 17, 1994

[30] Foreign Application Priority Data

Sep. 2, 1992 [GB] United Kingdom .................. 9218581

[51] Int. Cl.[6] ............................ B01D 37/00; B01D 36/00
[52] U.S. Cl. ........................... 210/806; 55/421; 210/188; 210/195.1; 210/252; 210/254; 210/257.1; 210/295; 210/435; 210/436; 210/472; 210/767; 604/406; 604/410
[58] Field of Search ................................. 210/767, 806, 210/188, 195.1, 195.2, 252, 254, 257.1, 258, 295, 435, 436, 472; 604/4, 5, 406, 408, 410; 55/410, 421

[56] References Cited

U.S. PATENT DOCUMENTS

| | | | |
|---|---|---|---|
| 3,000,540 | 9/1961 | Wheeler | 141/309 |
| 3,911,918 | 10/1975 | Turner . | |
| 4,223,695 | 9/1980 | Muetterties | 137/173 |
| 4,416,772 | 11/1983 | Sato et al. | 210/137 |
| 4,507,119 | 3/1985 | Spencer | 604/280 |
| 4,608,178 | 8/1986 | Johansson et al. | 210/744 |
| 4,857,190 | 8/1989 | Wada et al. | 210/232 |
| 4,985,153 | 1/1991 | Kuroda et al. | 210/782 |
| 4,997,577 | 3/1991 | Stewart | 210/767 |
| 5,053,127 | 10/1991 | Schoendorfer et al. | 210/196 |
| 5,071,570 | 12/1991 | Shiraki et al. | 210/774 |
| 5,100,564 | 3/1992 | Pall et al. | 210/782 |

(List continued on next page.)

FOREIGN PATENT DOCUMENTS

| | | |
|---|---|---|
| 0455215 | 11/1991 | European Pat. Off. . |
| 1585989 | 3/1981 | United Kingdom . |
| 9104088 | 4/1991 | WIPO . |
| 9117809 | 11/1991 | WIPO . |
| 9207656 | 5/1992 | WIPO . |

OTHER PUBLICATIONS

Kretschmer et al., "Improvement of Blood . . . New Bag System", Infusionstherapie, 15:232–239 (Jun. 1988).
Murphy, "Preparation and Storage of Platelet Concentrates", Principles of Transfusion Medicine, pp. 205–213 (1991).
Pietersz et al., "Preparation of Leukocyte–Poor . . . from Buffy Coats", Vox Sang., 53:208–213 (1987).

Primary Examiner—John Kim
Attorney, Agent, or Firm—Leydig, Voit & Mayer

[57] ABSTRACT

Methods and apparatuses for removing unwanted fluid such as gas from a processed blood product are disclosed. Methods include the steps of passing a blood product from a closed first container through a functional biomedical device to produce a processed blood product, flowing the processed blood product and an unwanted fluid from the functional biomedical device to a second container through a conduit, separating the unwanted fluid from the processed blood product in the second container, preventing the flow of the unwanted fluid from the second container through the passage to the functional biomedical device by using a clamp and passing the unwanted fluid from the second container to the first container through an outlet providing fluid communication between the second container and the first container. The outlet includes a barrier medium which allows the passage therethrough of the unwanted fluid but prevents the passage therethrough of the processed blood product.

31 Claims, 3 Drawing Sheets

U.S. PATENT DOCUMENTS

| | | | |
|---|---|---|---|
| 5,102,407 | 4/1992 | Carmen et al. | 604/410 |
| 5,126,054 | 6/1992 | Matkovich | 210/641 |
| 5,128,048 | 6/1992 | Stewart et al. | 210/749 |
| 5,152,905 | 10/1992 | Pall et al. | 210/767 |
| 5,180,504 | 1/1993 | Johnson et al. | 210/767 |
| 5,217,627 | 6/1993 | Pall et al. | 210/767 |
| 5,258,126 | 11/1993 | Pall et al. | 210/767 |
| 5,316,674 | 5/1994 | Pall et al. | 210/257.1 |
| 5,364,526 | 11/1994 | Matkovich et al. | 210/206 |
| 5,451,321 | 9/1995 | Matkovich | 210/641 |
| 5,472,621 | 12/1995 | Matkovich et al. | 210/767 |
| 5,512,187 | 4/1996 | Buchholz et al. | 210/767 |
| 5,527,472 | 6/1996 | Bellotti et al. | 210/767 |

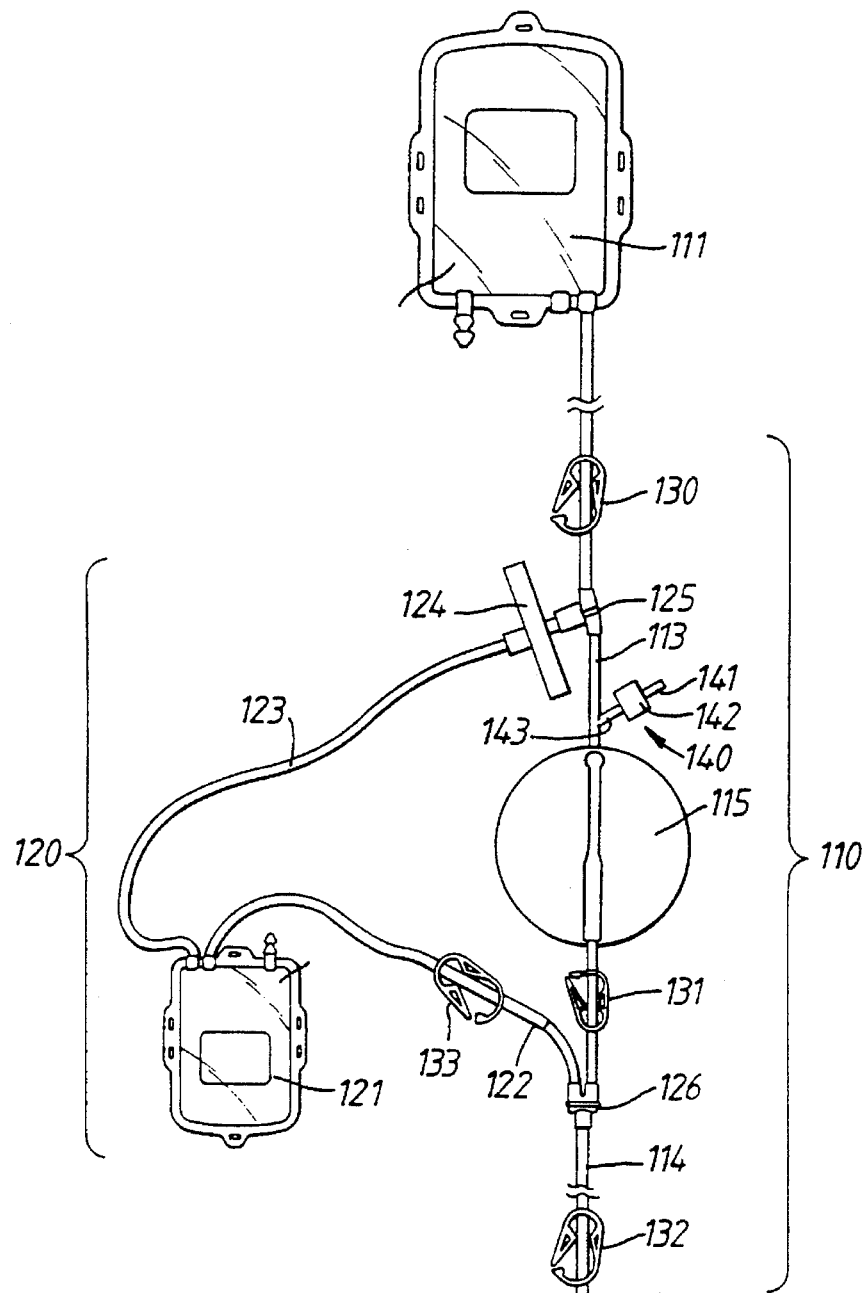
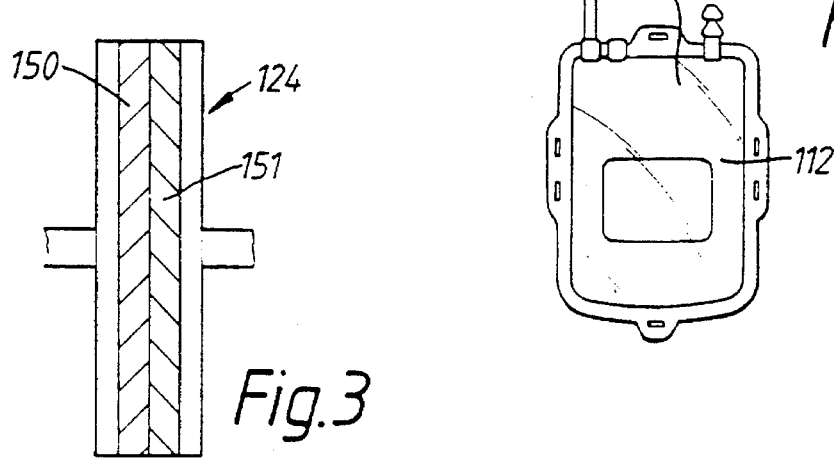
Fig.2
Fig.3

PROCESS AND APPARATUS FOR REMOVAL OF UNWANTED FLUIDS FROM PROCESSED BLOOD PRODUCTS

This application is an application filed under 35 U.S.C. 371 of PCT/GB93/01849 filed Sep. 1, 1993.

The invention relates to the removal of unwanted fluids from processed blood products.

As used herein, "blood product" refers to any treated or untreated fluid associated with living organisms, particularly blood, including whole blood, warm or cold blood, and stored or fresh blood; treated blood, such as blood diluted with a physiological solution, including but not limited to saline, nutrient, and/or anticoagulant solutions; one or more blood components, such as platelet concentrate (PC), platelet-rich plasma (PRP), platelet-free plasma, platelet-poor plasma, plasma, packed red cells (PRC), or buffy coat; analogous blood products derived from blood or a blood component or derived from bone marrow. The blood product may include leucocytes, or may be treated to remove leucocytes. As used herein, blood product refers to the components described above, and to similar blood products obtained by other means and with similar properties.

When a blood product is processed by a functional biological device there is a clinical risk of gases, including air, remaining in the processed blood product.

The sources of residual oases include the functional biological device performing the process and tubing used for passing the blood product to and from the device. There may also be gases present in the container to which the processed blood product is transferred.

The term "functional biomedical device", as used herein, may be any of a number of devices or assemblies in which air or gases are present and/or may collect or form, or should be displaced prior to use of the assembly. Exemplary functional biomedical devices include a filter, such as a leucocyte depletion filter; a separatory device, such as a platelet concentrator, preferably a non-centrifugal platelet concentrator; a debubbler; or a pump. The functional biomedical device may also include a device for destroying biological contaminants, such as a high intensity light wave chamber, or a device for sampling a biological liquid. Exemplary devices for use with red blood cells are disclosed in U.S. Pat. Nos. 4,925,572 and 4,923,620; an exemplary device for use with platelets is disclosed in U.S. Pat. No. 4,880,548. It is intended that the invention should not be limited by the type of functional biomedical device employed in a specific assembly.

The presence of such residual gases can reduce the quality of the biological fluid being stored and thus can reduce the time period for which the biological fluid can be stored. In addition, such gases reduce the storage capacity of the containers in which the blood product is held. In addition, such residual gases, on transfusion, may enter the recipient of the transfusion and result in embolism. The clinical consequences of this are well documented in the literature.

It is thus important to have as little gas as possible, ideally no gases, left in the processed blood product. Section IV 2.2.2.1 of the European Pharmocopoeia states that less than 5 ml of gases should remain in the container for processed blood product.

It is also important that any processing be wholly free from bacterial contamination from the environment.

It has previously been proposed to provide in the functional biomedical device, an outlet for the bleeding off of air collecting in the device. The vent may include a hydrophobic filter medium—see for example GB-A-1585989 which separates air from a filtered blood product. It is a problem with such a proposal that this deals only with air at or reaching the functional biomedical device. It does not remove air exiting the functional biomedical device with the processed blood product.

In another proposal, a by-pass line is provided between a first container for the unprocessed blood product (often called the "donor bag") and a second container receiving the processed blood product (often called the "transfer bag"). The by-pass line by-passes the functional biomedical device and includes a clamp or breakaway valve or both, for isolating the by-pass line.

After the blood product has been processed from the donor bag, gases in the transfer bag are moved to the now empty donor bag through the by-pass loop, after the clamp/breakaway valve has been opened. The transfer bag is either squeezed by hand or placed in a plasma expresser to drive the gases through the by-pass loop. During this by-pass, the functional biomedical device is isolated.

A problem with this proposal is a significant risk of blood product breaking past the clamp/breakaway valve in the by-pass if this is broken/malfunctional before use or if it is accidentally left open. The consequence of this is that the processed blood product may well be contaminated with a volume of unprocessed blood product. For example, if the processing is the reduction of leukocytes in a blood product, then there will be in the processed blood product a higher level than desired of such leukocytes.

In an alternative proposal, a device is provided in the passage between the functional biomedical device and the transfer bag which includes a bacterially secure outlet or vent filter. Thus, gases in front of the blood product are displaced through the outlet or filter to atmosphere during the processing of the blood product. These gases can be stored and returned to the system to facilitate recovery of the blood product.

This, however, does not remove gases already in the transfer bag which can account for 50% of the total volume of gases that can accumulate in the transfer bag.

A third proposal, used where the functional biological device is a leukocyte filter, is to squeeze the transfer bag to pass accumulated gases from the transfer bag back through the leukocyte filter into the donor bag. This is, however, unreliable as a minimum pressure has to be applied to the transfer bag to overcome the bubble point of filter medium in the leukocyte filter to move gases out of the transfer bag. This is operator-dependent and may not be achieved successfully every time. Further, if squeezing is stopped and restarted there is a risk of displacing retained contaminants from the leukocyte filter into the processed blood product.

Similar problems can arise in the removal of supernatent liquids from red cell washing and centrifuging of blood products. This supernatent liquid is an unwanted fluid that must be discarded prior to use.

According to a first aspect of the invention, there is provided a method of removing unwanted fluid from a processed blood product comprising passing the blood product from a closed first container through a functional biomedical device to process the blood product, flowing the processed blood product and the unwanted fluid from the functional biomedical device, separating the unwanted fluid from the processed blood product and passing the unwanted fluid through an outlet including a barrier medium which allows the passage therethrough of the unwanted fluid but prevents the passage therethrough of the processed blood product.

According to a second aspect of the invention, there is provided apparatus for removing an unwanted fluid from processed blood product comprising a first container for holding blood product to be processed, a first passage connecting the first container to a functional biomedical device and a second passage leading from said functional biomedical device, characterised in that an outlet passage leads to the first passage or the first container and includes a barrier medium for preventing the passage therethrough of processed blood product but allowing the passage of unwanted fluid to the first container.

Figure 4:
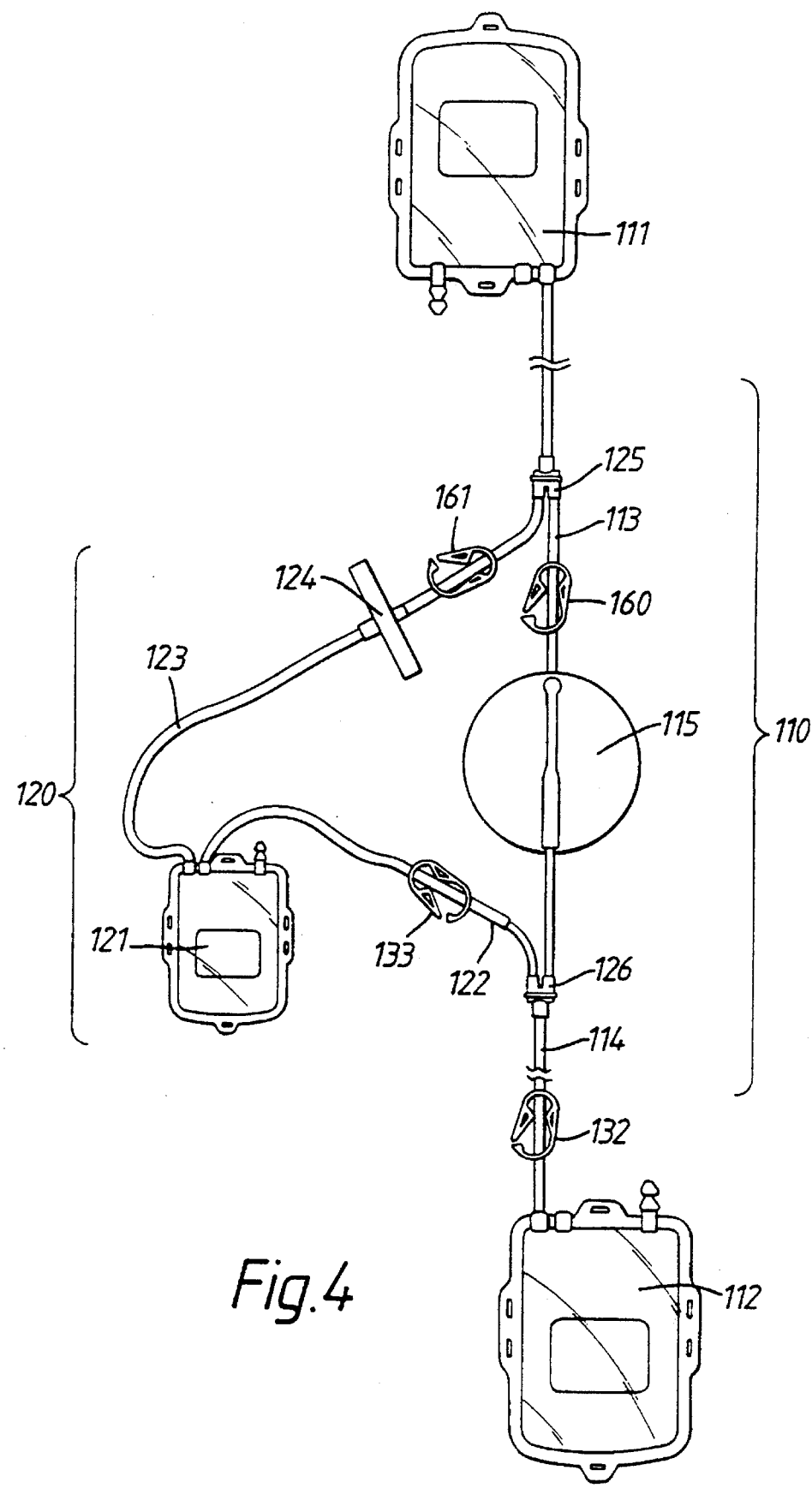

The following is a more detailed description of some embodiments of the invention, by way of example, reference being made to the accompanying drawings in which:

FIG. 1 is a schematic diagram of an apparatus for depleting the leukocyte content of a blood product and including a filter for use in removing air from the processed blood product, FIG. 2 is a schematic view of an apparatus for processing a blood product and including a filter for use in the removal of air from the processed blood product, FIG. 3 is a schematic cross-sectioned view of an embodiment of a liquid barrier medium for use in the apparatus of FIG. 2, and FIG. 4 is a schematic view of another apparatus for processing a blood product and including a filter for use in the removal of air from the processed blood product.

The apparatus of FIG. 1, comprises a closed first container in the form of a donor bag 10 for containing a blood product such as red cells or whole blood or platelets. A tube 11 leads from the donor bag 10 to a functional biological device in the form of a leukocyte depleting blood filter 12, which may be of the kind described in GB-A-2211755.

The outlet to the filter 12 is connected by a tube 13 to a second container in the form of a closed transfer bag 14. A manually operable clamp 15 is provided on this tube 13 to allow the tube 13 to be opened and closed. As an alternative, a check value could be provided.

An outlet tube 16 leads from the transfer bag 14 to the donor bag 10 and includes a filter 17. The filter 17 is a hydrophobic filter having a pore rating sufficient to separate gas, such as oxygen air or the like, that may be present in a blood processing system, from the liquid i.e. blood or blood components that are processed in the system. Such a pore rating maybe less than 5 μm and preferably 0.2 μm or 0.1 μm. A manually operable clamp 18 is provided in the line 15 between the filter 17 and the tube 11 for opening and closing the line 15.

In use, initially the clamp 15 is opened and the clamp 18 is closed. A donor bag 10 containing, for example, whole blood, is connected to the tube 11. The leukocyte filter 12 is primed by squeezing the donor bag 10 and the blood passes through the filter 12 to the transfer bag 14. At the end of the transfer, the clamp 15 is closed and residual leukocyte-depeted blood product in the tube between the clamp 15 and the transfer bag 14 is stripped into the transfer bag 14.

At this point, the transfer bag 14 is filled with leukocyte-depleted blood and air. The source of this air includes the filter 12 and residual air in the transfer bag 14.

The transfer bag 14 is then hand squeezed or placed in a plasma expresser (not shown) and the clamp 18 is opened. The air in the transfer bag is thus passed through the tube 16 to the filter 17. The filter 17 has a pore size which allows the passage through the filter 17 of air, but prevents the passage of processed blood. As mentioned above, this is generally less than 5 μm and may be 0.2 μm or 0.1 μm.

The air passes from the filter 17 to the donor bag 10 and when all the air has been expelled from the transfer bag 14, the clamp 18 is closed and the clamp 15 is opened. The air in the donor bag 10 will then pass into the tube 11 and displace blood in the tube 11 and the leukocyte filter 12 to the transfer bag 14, without air entering the transfer bag 14.

The transfer bag 14 is then separated from the tube 13 and the tube 16.

The apparatus has the advantage that, in use, it is completely closed so allowing the processing and air removal to be wholly free of bacterial contamination from the environment. If, when the blood product is being processed, blood product should pass the clamp 18, the filter 17 will prevent the passage of the blood product to the transfer bag 14.

In addition, since air is displaced from the transfer bag 14 after processing, all of the air can be removed. The operation is quick and can be performed rapidly. The only additional equipment required, a tube stripper and a plasma expresser, are readily available in the circumstances in which the apparatus is used.

The air is not passed through the leukocyte filter 12 during its removal and so it does not suffer from the problems associated with displacing air through a used leukocyte filter.

A similar apparatus and method can be used for removing other unwanted fluids from processed blood products. For example, supernatant liquids may be removed from the product of red cell washing and centrifugation. In this case, and where the liquid is a miscible liquid, the filter 17 will be a hydrophilic filter which may have a pore size of less than 5 μm, preferably 0.1 μm or 0.2 μm. Where the liquid is immiscible, the filter 17 will be a hydrophobic filter which may have a pore size of less than 5 μm, preferably 0.1 μm or 0.2 μm.

The apparatus and method described above with reference to FIG. 1 need not be used in conjunction with a functional biological device (such as the leukocyte filter 12 described above). The tube 16 may be used only in conjunction with a transfer bag 14, or its equivalent, containing a processed blood product.

A second embodiment of the invention will now be described by reference to FIG. 2. FIG. 2 shows a blood processing assembly which includes a first container or donor bag 111 and a second container or transfer bag 112, and a conduit 113,114 interconnecting the first container 111 with the second container 112; and having interposed between the first container 111 and the second container 112, at least one functional biomedical device 115. The functional biomedical device 115 may be associated with a vent filter 140. The vent filter 140 includes an inlet 141 for ambient air, a filter medium 142 for removing bacterial matter from the air and an outlet 143 connected to an inlet of the functional biomedical device 115 to supply sterile air to the inlet to displace blood product through the assembly.

A gas collection and displacement loop 120 is in fluid communication with the first conduit 113 and the second conduit 114.

The loop 120 is a flow path for separating gas from the biological fluid flow path, and, optionally, using that collected gas to recover additional biological fluid. The loop 120 includes a conduit 122 in fluid communication with the second container 112 and a conduit 123 in fluid communication with the first container 111. Fluid communication for each conduit 122 123 may be established by any type of junction 126 and 125, respectively. As illustrated, junction 126 is a Y-type junction and junction 125 is a flexible T-type junction.

The gas collection and displacement loop 120 includes a third container 121 interposed between the conduit 122 and the conduit 123. The third container 121 is used for collecting and storing the displaced gas. The third container 121 is a flexible bag which can be squeezed in order to transfer gas in third container 121 into the first container 111 and/or the conduit 113. Other arrangements are possible; for example, the conduits 122 and 123 may be attached to a syringe, or the like, which could draw gas from the processing assembly into the conduit 122 and could transfer the collected gas in the syringe into the first container 111 and/or conduit 113. It is intended that the gas collection and displacement loop functions so that leukocyte-laden fluid is barred from contacting leukocyte depleted fluid.

The gas collection and displacement loop 120 also includes a liquid barrier medium 124 located in the conduit 123 between the third container 121 and the junction 125.

The liquid barrier medium 124 may be any of a variety of means and devices which are capable of separating gas such as air, oxygen and the like, that may be present in a blood processing system from the liquid, i.e., blood and/or blood components that are processed in the system. Suitable liquid barrier media include, but are not limited to, those disclosed in International Publication No. WO 91/17809.

The liquid barrier medium is particularly suited for use in closed and/or sterile systems. Suitable liquid barrier media include a liquophobic porous medium. In some embodiments, liquid barrier media include a sufficiently small pore size to preclude the passage of bacteria through the liquid barrier medium. Because such a liquophobic porous medium is not wettable by the biological fluid being processed in the system, gas in the system that contacts the liquophobic medium will pass through it and the blood product will not be absorbed by the liquophobic porous medium. In some embodiments, the pore size of the liquophobic porous medium will be 0.2 μm or less to provide a satisfactory bacterial barrier.

The term "liquophobic" as used herein is effectively the obverse of the term liquophilic; that is, a porous liquophobic material has a critical wetting surface tension lower than the surface tension of the applied liquid and is not readily or spontaneously wetted by the applied liquid. Liquophobic materials may be characterized, then, by a high contact angle between a drop of liquid placed on the surface, and the surface. Such high contact angle indicates poor wetting.

The liquid barrier medium may comprise a liquophobic membrane as described above, or may comprise other structures which allow gas to pass, but do not allow contaminants to enter. In an embodiment, shown in FIG. 3, the liquid barrier medium 124 includes a multi-layer microporous membrane in a housing. The first layer 150 of the microporous membrane may be liquid-wettable, i.e., liquophilic. The liquophilic membrane is capable of passing gas therethrough so long as it remains unsaturated by the liquid being processed. The second microporous membrane layer 151 is not wettable by the liquid being processed by the delivery system, that is, the second layer is liquophobic. Exemplary liquophilic and/or liquophobic media include those disclosed in International Publication No. WO 91/17809.

The liquophilic layer 150 of the multi-layer microporous membrane is preferably positioned in the housing to the inward side of the liquid barrier medium. In this way the liquophilic layer 150 is the first layer to be contacted either by gas that is to be passed from the liquid transfer or delivery system or by the liquid being transferred or delivered by the system.

The liquophobic layer 151 is also capable of passing gas therethrough. The liquophobic layer 151 may be superimposed on the liquophilic layer 150, preferably positioned on the outward side of the liquid barrier medium. Because of the liquid-wettable character of liquophilic layer 150 and the non-wettable character of liquophobic layer 151, gas that contacts the liquid barrier medium passes through the liquid barrier medium so long as the liquophilic layer 150 remains unwetted by liquid. Once the liquophilic layer 150 becomes wetted with liquid, gas is no longer able to pass through the liquophilic layer 150 so that the liquid barrier medium becomes sealed or inactivated. The combined liquophobic and liquophilic membrane 150,151 is particularly advantageous when the liquid barrier medium is used in a closed sterile system.

It will be appreciated that the liquophilic and liquophobic layers 150,151 may be two separate layers, or they may be bonded together. In addition, a plurality of separate membrane elements could be combined together to form the liquophilic microporous membrane 150 and a plurality of separate membrane elements combined together to form the liquophobic microporous membrane 151. By the term plurality is meant two or more. The plurality of separate membrane layers may be individually prepared and bonded together by various means known to those skilled in the art. For example, the separate membrane layers may be bonded together by drying two or more layers maintained in close contact. Alternatively, by way of illustration and not in limitation, the separate membrane layers may be prepared by passing the material used to form the membrane over a hot drum, against which the membrane is firmly held by a tensioned felt web or other process sheet. In addition, it is likewise possible to combine a suitable supporting substrate with the membrane layer, if desired, and the supporting substrate may serve as a permanent support.

The liquophobic miroporous membrane 151 must have sufficient liquophobicity with respect to the liquid to be processed such that it will prevent the intrusion of the liquid being processed into the membrane. On the other hand the liquophilic microporous membrane 150 must have a pore size and sufficient liquophilicity with respect to the liquid to be processed such that it will be wetted by the liquid sufficiently to prevent the passage of gas after it is wetted. In an embodiment, both the liquophilic and liquophobic microporous membranes 150,151 have, when combined for use in the liquid barrier medium, an overall pore size such that the membranes form a bacterial barrier. Preferably, particularly in medical applications, the system is gamma-sterilizable.

The microporous membrane may be made from a variety of materials provided the requisite properties of the particular porous medium are achieved. These include the necessary strength to handle the differential pressures encountered in use and the ability to provide the desired filtration rapability while providing the desired permeability without the application of excessive pressure. The porous medium may be, for example, a porous fibrous medium, such as a depth filter, or a porous membrane or sheet. Multilayered porous media may be used, for example, a multilayered porous membrane with one layer being liquophobic and the other liquophilic.

Preferred starting materials are synthetic polymers including polyamides, polyesters, polyolefins, particularly polypropylene and polymethylpentene, perfluorinate, polyolefins, such as polytetrafluoroethylene, polysulfones, polyvinylidene difluoride, polyacrylonitrile and the like, and compatible mixtures of polymers. The most preferred polymer is polyvinylidene difluoride. Within the class of polyamides, the preferred polymers include polyhexamethylene adipamide, poly-ε-caprolactam, polymethylene sebacamide, poly-7-aminoheptanoamide, polytetramethylene adipamide (nylon 46), or polyhexamethylene azeleamide, with polyhexamethylene adipamide (nylon 66) being most preferred. Particularly preferred are skinless, substantially alcoholinsoluble, hydrophilic polyamide membranes, such as those described in U.S. Pat. No. 4,340,479.

Other starting materials may also be used to form the porous media of this invention including cellulosic derivatives, such as cellulose acetate, cellulose propionate, cellulose acetate-propionate, cellulose acetate-butyrate, and cellulose butyrate. Non-resinous materials, such as glass fibres, may also be used.

It will be appreciated that if the material chosen is normally liquophobic, and it is desired to use this material for the liquophilic microporous membrane, then the normally liquophobic material will have to be treated so as to make it liquophilic. The nature of the material used to make the membranes, the compatibility of the materials chosen for the membranes with one another and with the liquid to be processed all are factors to be considered in selecting a particular material for a membrane for a given end application. However, quite apart from those considerations, it may be desirable that the same material be used for both the liquophilic microporous membrane and for the liquophobic microporous membrane so as to facilitate the bonding of the two different membranes to one another, if desired, as is preferred.

The preferred materials for the liquophilic microporous membrane and the liquophobic microporous membrane are nylon and polyvinylidene difluoride, respectively. Since polyvinylidene difluoride is liquophobic, it must be treated in order to render it liquophilic. Various treatments of the normally liquophobic polyvinylidene difluoride to render it liquophilic are known. However, the preferred method for making the polyvinylidene difluoride material liquophilic is to treat a liquophobic polyvinylidene difluoride microporous membrane by subjecting it to gamma radiation in the presence of a liquophilic agent, such as, for example, hydroxyethylmethacrylate (HEMA), Alternatively, the polyvinylidene difluoride material may be treated by a gas plasma process to render it liquophilic. Examples of such a gas plasma process are shown in U.S. Pat. Nos. 4,261,806 and 4,948,628. Preferably liquophilic and liquophobic polyvinylidene microporous membranes are secured to each other by placing them in intimate contact and drying them on a drum dryer.

The rate of air flow through the microporous membrane of a liquid barrier medium can be tailored to the specific liquid transfer or delivery system of interest. The rate of air flow varies directly with the area of the membrane and the applied pressure. Generally, the area of the membrane is designed to enable the liquid transfer or delivery system to be primed in a required time under the conditions of use. In such applications as well as in other medical applications, the typical membrane may be in the form of a disc which has a diameter from about 1 mm to about 100 mm, preferably from about 2 mm to about 80 mm, and more preferably from about 3 mm to about 25 mm.

The pore size of the liquophilic and liquophobic microporous membranes is dependent on the system in which it is used, and, more particularly, whether the system is for medical or non-medical use. The pore size of the liquophilic and liquophobic microporous membranes may be the same or different. Generally the pore size of the liquophobic membrane is in the range of from about 0.02 µm to about 3 µm and the pore size of the liquophilic membrane is from about 0.04 µm to about 3 µm. It will be appreciated that the pressure required to transfer gas through the liquid barrier medium of the system described above varies inversely with the pore size of the membrane. Accordingly, the choice of pore size may be determined by the application in which the liquid barrier medium is used. For example, since the pressure required to pass gas through the liquid barrier medium increases as the pore size of the membrane decreases, it maybe desirable to choose a larger pore size (consistent with the other objectives of, for example, providing a bacterial barrier and/or a suitable flow rate) where the delivery system is to be operated by hand so that the pressure required to use the system does not become too great for convenient hand use and/or so that the flow rate is suitable for using the system within an acceptable time frame.

A liquid barrier medium 124 may be included in any of the various elements of the assembly. By way of illustration, a liquid barrier medium may be included in at least one of the conduits which connect the different containers, in a wall of the containers that receive the processed blood and/or blood product, or in a port on or in one of those containers. A liquid barrier medium may also De included on or in a combination of the elements mentioned above. Also, the functional biomedical device may include one or more liquid barrier media.

It will be apparent to one skilled in the art that the placement of a liquid barrier medium may be optimized to achieve a desired result. For example, it may be desirable to locate the liquid barrier medium as close to junction 125 as is practical. In a more preferred embodiment, a clamp may be located between the liquid barrier medium 124 and the junction 125, as exemplified in FIG. 4.

As seen in FIG. 2, the assembly includes four clamps. A first clamp 130 is provided in the conduit 113 between the first container 111 and the junction 125. A second clamp 131 is provided between the functional biomedical device 115 and the junction 126 and a third clamp 132 is provided between the junction 126 and the second container 112. Finally a fourth clamp 133 is provided in the conduit 122 between the junction 126 and the third container 121. In another embodiment, as seen in FIG. 4, clamp 160 is located on conduit 113 between junction 125 and functional biomedical device 115. Clamp 161 is located on a conduit between liquid barrier medium 124 and junction 125. Clamp 132 is provided between the junction 126 and the second container 112, and clamp 133 is provided on the conduit between junction 126 and the third container 121. The use in the clamps shown in FIG. 2 is described below.

Recovery from the various elements of the processing assembly may be maximized.

The housing may be constructed of rigid plastic material that is also transparent, such as polyethylene, an acrylic such as polymethyl methacrylate, polymethyl acrylate, polymethyl pentene-1, polyvinyl chloride, and vinyl chloride-vinylidene chloride copolymers. Translucent materials, such as polypropylene, polyethylene, urea-formaldehyde, and melamine-formaldehyde polymers, can also be employed. Other plastic materials that are particularly suitable are polystyrene, polyamides, polytetrafluoroethylene, polyfluorotrichloroethylene, polycarbonates, polyester, phenol-formaldehyde resins, polyvinyl butyral, cellulose acetate, cellulose acetate propionate, ethyl cellulose and polyoxymethylene resins. Polyacrylonitrile polybutadiene-styrene (ABS) is preferred. It is intended that the invention should not be limited by the type of housing being employed; other materials may be used, as well as mixtures, blends, and/or copolymers of any of the above.

A metal housing can be used. Suitable metals include stainless alloys, such as nickel, chromium, vanadium, molybdenum, and manganese alloys. The housing material should, of course, be inert to the liquids being processed.

The containers which are used in the blood processing assembly may be constructed of any material compatible with whole blood or blood products, and are capable of withstanding a centrifugation and sterilization environment. A wide variety of these containers are already known in the art. For example, blood collection and satellite bags are typically made from plasticized polyvinyl chloride, e.g., PVC plasticized with dioctylphthalate, diethylhexylphthalate, or trioctyltrimellitate. The bags may also be formed from a polyolefin, polyurethane, polyester, or polycarbonate.

The assembly described above with reference to FIG. 2 is used in the following way. Movement of blood or a blood product through the assembly is effected by maintaining a pressure differential between the first container 111 and the destination of the blood or the blood product. Exemplary means of establishing this pressure differential may be by gravity head, applying pressure to the collection bag (e.g., by hand or with a pressure cuff), or by placing the second container 112 in a chamber which establishes a pressure differential between the first container 111 and the second container 112 (e.g., a vacuum chamber).

Once the pressure differential is established and clamps 130,131, and 133 are opened and clamp 132 is closed, a column of blood product is driven through conduit 113, through functional biomedical device 115, into conduit 114, until the blood product reaches junction 126. As the blood product advances, it pushes gas in the conduit ahead of it until the gas reaches junction 126. At junction 126, gas ahead of the blood product moves into the gas collection and displacement loop 120. Once all gas has passed into the loop 120, clamp 133 is then closed, clamp 132 is opened, and biological fluid flows into second container or transfer bag 112.

The gases that pass into the gas collection and displacement loop 120 are collected in the third container 121 and returned to the system as a purge gas to facilitate the recovery of biological fluid that becomes trapped in the various components of the system. This is achieved in the following way.

After the blood in collection bag 111 is processed, the clamp 132 is closed, and the third container 121 is compressed to feed the gas in the container 121 as a purge gas into the system through conduits 123 and 113. The gas passes through liquid barrier medium 124 in conduit 123 and then passes through the conduit 113 into the first container 111. After opening clamp 132, gas from the first container 111 will then displace any biological product remaining in the first container 111, the conduit 113, and the functional biomedical device 115 into the second container 112. Optionally, first container 111 may be squeezed so to assist this recovery.

Once recovery is complete, the clamp 131 may be closed, the clamp 133 may be opened, and the second container 112 may be squeezed in order to remove any gas from the second container 112. At the completion of gas removal from the second container 112, the clamp 132 should be closed.

In another embodiment, the assembly includes a pre-primed functional biomedical device.

It will be appreciated that, although the third container 121 is described above as being formed by a flexible bag, the container 121 may be a rigid container. In addition, although the third container 121, the liquid barrier medium 124 and means for closing the loop (the fourth clamp 133) are described above as separately formed, they may be formed as an integral unit.

Of course, air in the second container 112 may be removed by closing the clamp 131 and opening the clamps 132 and 133. The second container 112 can then be squeezed in any one of the ways described above to pass air through the conduit 114 to the conduit 122 and thence to the container 121. From the container 121, the air can be passed to the container 111 as described above with reference to FIG. 2.

In another embodiment shown in FIG. 4, including a liquid barrier medium 124, and a third container 121 (hereinafter the gas collection and displacement bag), a functional biomedical device 115 may be connected to a second container 112, and a gas collection and displacement loop 120 may be connected upstream and downstream of the functional biomedical device. The gas collection and displacement loop may be connected using Y-connectors upstream 125 and downstream 126 of the functional biomedical device 115. The gas collection and displacement loop includes a 100 cc gas collection and displacement bag 121 and a housing containing a liquid barrier medium. The housing and liquid barrier medium formed a liquid barrier assembly 124. The liquid barrier assembly is located within the gas collection and displacement loop in a conduit between the Y-connector 125 upstream of the functional biomedical device 115 and the gas collection and displacement bag. The liquid barrier medium includes a liquophobic membrane produced in accordance with International Publication No. WO 91/17809. The liquid barrier assembly was also produced in accordance with International Publication No. WO 91/17809.

There may be a clamp 160 on the conduit between the upstream of the functional biomedical device 115 and the connector 125, as well as a clamp 161 on the conduit between the connector 125 upstream of the functional biomedical device and the liquid barrier medium 124. There may also be a clamp 133 on the conduit between the gas collection and displacement bag 121 and the connector downstream of the functional biomedical device 126, as well as a clamp 132 on the conduit between the downstream of the functional biomedical device and the satellite bag 112. This clamp 132 may be located downstream of the connector 126 that connects the downstream of the functional biomedical device to the gas collection and displacement loop.

Clamps 160,161,133 and 132 may be closed, and the first container may be connected to the conduit upstream of the functional biomedical device. The functional biomedical device may be positioned vertically. Clamps 160 and 132 may be opened and the blood product may be expressed from the first container 111 through the functional biomedical device 115 into the second, or satellite, container 112 until the first container is drained. Gas may be displaced by the blood product into the second container. Clamp 160 may then be closed.

The gas collection and displacement bag 121 may be raised and clamp 133 should be opened. Raising the gas collection bag may allow additional blood product in the conduit downstream of the functional biomedical device to drain into the satellite container. Once the fluid has drained, clamp 133 may be closed and the gas collection and displacement bag may be lowered. Then the satellite container 112 should be manipulated until gas collects toward the upper portion of the satellite container. Clamp 133 should then be opened while continuing to compress the satellite bag to expel gas from the satellite container into the gas collection and displacement bag 121. Once the gas has been expelled, clamp 133 should be closed.

The gas collection and displacement bag 121 may be manipulated until gas collects toward the upper portion of the gas collection bag and the tubing. Clamp 161 may be opened, and gas may be passed into the conduit upstream of the functional biomedical device and possibly into the first container, and then clamp 161 may be closed. Clamp 160 may then be opened, which may displace or "chase" some of the blood product retained in the functional biomedical device and/or the conduit downstream of the functional biomedical device. This displaced blood product may be recovered in the satellite container 112 without collecting gas, since the functional biomedical device 115 will not completely drain.

Clamp 132 should then be closed, and the tubing from the outlet side of the functional biomedical device should be sealed.

We claim:

1. A method of removing unwanted fluid from a processed blood product comprising:

passing a blood product from a closed first container through a functional biomedical device to produce a processed blood product;

flowing the processed blood product and an unwanted fluid from the functional biomedical device to a second container through a passage;

separating the unwanted fluid from the processed blood product in the second container;

preventing the flow of the unwanted fluid from the second container through the passage to the functional biomedical device; and passing the unwanted fluid from the second container to the first container through an outlet providing fluid communication between the second container and the first container, said outlet including a barrier medium which allows the passage therethrough of the unwanted fluid but prevents the passage therethrough of the processed blood product.

2. A method according to claim 1, wherein the unwanted fluid is a gas, the gas being filtered through a barrier medium in the form of a liquophobic filter to prevent the passage therethrough of processed blood product.

3. A method according to claim 1, wherein the unwanted fluid is a miscible liquid, the miscible liquid being filtered through a barrier medium comprising a liquophilic filter having a pore size sufficient to allow the passage therethrough of said miscible liquid but to prevent the passage therethrough of processed blood product.

4. A method according to claim 1, wherein the unwanted fluid is an immiscible liquid, the liquid being filtered through a barrier medium in the form of a liquophobic filter having a pore size sufficient to allow the passage therethrough of said immiscible liquid but to prevent the passage therethrough of the processed blood product.

5. A method according to claim 1, wherein the unwanted fluid is a gas, the gas being filtered through a barrier medium including at least one liquophilic filter and at least one liquophobic filter arranged in succession in the path of flow of the gas therethrough, the at least one liquophilic filter allowing said gas to pass therethrough until the liquophilic filter is wetted and the at least one liquophobic filter preventing the passage therethrough of the processed blood product.

6. A method according to claim 1, wherein said outlet comprises a branch from said passage, and wherein flow of the unwanted fluid to said functional biomedical device via said passage is prevented while the unwanted fluid is passed through the barrier medium.

7. A method according to claim 6, wherein said outlet is closed while said blood product is processed.

8. A method according to claim 1, wherein the unwanted fluid is a gas, the method further comprising passing said gas collected in said first container from the first container through said functional biomedical device to expel additional processed blood product from said functional biomedical device.

9. A method according to claim 1, wherein the unwanted fluid is passed from the second container to a third container wherein said unwanted fluid is stored before being passed to the first container.

10. A method according to claim 1, wherein the unwanted fluid is passed directly to the first container from the second container through said barrier medium.

11. A method according to claim 1, wherein the step of passing the blood product through a functional biomedical device further comprises passing the blood product through a leucocyte-depleting filter.

12. The method according to claim 1, including preventing the flow of blood product from the first container through the outlet to the second container while said blood product is processed.

13. Apparatus for removing an unwanted fluid from a processed blood product comprising:

a first container for holding blood product to be processed;

a conduit comprising a first portion connecting the first container to a functional biomedical device and a second portion leading from said functional biomedical device to a second container for holding processed blood product;

an outlet passage leading from the second container to the first container and including a barrier medium for preventing the passage therethrough of processed blood product but allowing the passage of unwanted fluid to the first container; and wherein said conduit comprises means positioned for closing said conduit during the passage through the outlet passage of the unwanted fluid to the first container to prevent the passage of unwanted fluid to said functional biomedical device.

14. Apparatus according to claim 13, wherein the unwanted fluid is a gas, the barrier medium being a liquophobic filter that permits the passage therethrough of said gas but prevents the passage therethrough of processed blood product.

15. Apparatus according to claim 11, wherein the liquophobic filter has a pore size of less than 5 µm.

16. The apparatus according to claim 15, wherein the liquophobic filter has a pore size in the range from 0.2 µm to 0.1 µm.

17. Apparatus according to claim 13, wherein the unwanted fluid is a miscible liquid, the barrier medium being a liquophilic filter having a pore size sufficient to allow the passage therethrough of said miscible liquid but sufficient to prevent the passage therethrough of processed blood product.

18. Apparatus according to claim 17, wherein the liquophilic filter has a pore size of less than 5 µm.

19. The apparatus according to claim 18, wherein the liquophilic filter has a pore size in the range from 0.2 µm to 0.1 µm.

20. Apparatus according to claim 13, wherein the unwanted fluid is an immiscible liquid, the barrier medium being a liquophobic filter having a pore size sufficient to allow the passage therethrough of said immiscible liquid but to prevent the passage therethrough of the processed blood product.

21. Apparatus according to claim 20, wherein the liquophobic filter has a pore size of less than 5 μm.

22. The apparatus of claim 21, wherein the liquophobic filter has a pore size in the range from 0.2 μm to 0.1 μm.

23. Apparatus according to claim 13, wherein the unwanted fluid is a gas, the barrier medium comprising at least one liquophilic filter and at least one liquophobic filter arranged in succession in the path of flow of the gas therethrough, the at least one liquophilic filter allowing said gas to pass therethrough until the liquophilic filter is wetted and the at least one liquophobic filter preventing the passage therethrough of the processed blood product.

24. Apparatus according to claim 23, wherein the pore size of the at least one liquophilic filter is in the range of from about 3 μm to about 0.04 μm and the pore size of the at least one liquophobic filter is in the range from about 3 μm to about 0.02 μm.

25. Apparatus according to claim 13, wherein the outlet passage branches from said second portion and leads to the first container.

26. Apparatus according to claim 13, wherein the outlet passage includes a storage container for storing said unwanted fluid before said unwanted fluid is passed to said first container.

27. Apparatus according to claim 13, wherein the outlet passage is uninterrupted along the length thereof other than by the barrier medium.

28. Apparatus according to claim 13, further comprising a clamp for closing said outlet passage during the passage of the blood product through said functional biomedical device.

29. Apparatus according to claim 13, further comprising a clamp in said outlet passage downstream of said barrier medium for closing said outlet passage.

30. Apparatus according to claim 13, including a connection between the outlet passage and the first portion of the conduit between the first container and the functional biomedical device, and further comprising a clamp for closing said first portion between said connection and said functional biomedical device.

31. Apparatus according to claim 13, wherein in that the functional biomedical device is a leukocyte-depleting filter.

* * * * *

UNITED STATES PATENT AND TRADEMARK OFFICE
CERTIFICATE OF CORRECTION

PATENT NO. : 5,601,730
DATED : February 11, 1997
INVENTOR(S) : Page et al.

It is certified that error appears in the above-identified patent and that said Letters Patent is hereby corrected as shown below:

Title page,
Item 30, change "9218581" to --9218581.8--;

Title page,
Item 56, Line 2, change "10/1975" to --11/1983--;

Column 11, Line 40, change "in the form of" to --comprising--;

Line 50, change "in the form of" to --comprising--;

Signed and Sealed this

Twenty-first Day of October 1997

Attest:

BRUCE LEHMAN

Attesting Officer

Commissioner of Patents and Trademarks